United States Patent
Burton

(10) Patent No.: US 10,099,934 B2
(45) Date of Patent: Oct. 16, 2018

(54) MOLECULAR SIEVE, COK-5, ITS SYNTHESIS AND USE

(71) Applicant: ExxonMobil Chemical Patents Inc., Baytown, TX (US)

(72) Inventor: Allen W. Burton, Stewartsville, NJ (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 476 days.

(21) Appl. No.: 14/782,407

(22) PCT Filed: Mar. 4, 2014

(86) PCT No.: PCT/US2014/020140
§ 371 (c)(1),
(2) Date: Oct. 5, 2015

(87) PCT Pub. No.: WO2014/172024
PCT Pub. Date: Oct. 23, 2014

(65) Prior Publication Data
US 2016/0023914 A1    Jan. 28, 2016

Related U.S. Application Data

(60) Provisional application No. 61/813,940, filed on Apr. 19, 2013.

(30) Foreign Application Priority Data

Jun. 17, 2013   (EP) ..................................... 13172271

(51) Int. Cl.
| | |
|---|---|
| *C01B 39/48* | (2006.01) |
| *C01B 39/08* | (2006.01) |
| *C01B 39/12* | (2006.01) |
| *B01J 20/18* | (2006.01) |
| *B01J 20/30* | (2006.01) |
| *B01J 29/70* | (2006.01) |
| *B01J 37/08* | (2006.01) |
| *C07D 207/06* | (2006.01) |

(52) U.S. Cl.
CPC .............. *C01B 39/48* (2013.01); *B01J 20/18* (2013.01); *B01J 20/3078* (2013.01); *B01J 29/70* (2013.01); *B01J 37/08* (2013.01); *C01B 39/08* (2013.01); *C01B 39/12* (2013.01); *C07D 207/06* (2013.01)

(58) Field of Classification Search
CPC ........ B01J 20/18; B01J 20/3078; B01J 29/70; B01J 37/08; C01B 39/08; C01B 39/12; C01B 39/48; C07D 207/06
See application file for complete search history.

(56) References Cited

U.S. PATENT DOCUMENTS

| | | | |
|---|---|---|---|
| 4,873,067 | A | 10/1989 | Valyocsik et al. |
| 2009/0104112 | A1 | 4/2009 | Burton |

FOREIGN PATENT DOCUMENTS

| | | |
|---|---|---|
| EP | 0135658 A2 | 4/1985 |
| WO | 2002/46099 | 6/2002 |
| WO | 2013/019462 | 2/2013 |

OTHER PUBLICATIONS

Jackowski, A. et al.,"*Diquaternary Ammonium Compounds in Zeolite Synthesis: Cyclic and Polycyclic N-Heterocycles Connected by Methylene Chains*," Journal of the American Chemical Society, ACS Publications, US, vol. 131, pp. 1092-1100 (2009).
Kirschhock, C. et al., "*Characterization of COK-5, Member of a New Family of Zeolite Material with Multiple Channel Systems*," Chem. Mater., vol. 17, pp. 5618-5624 (2005).
Liao, X. et al., "*Synthesis, Characterization of COK-5 with different Si/Al ratios and their catalytic properties for the tert-butylation of phenol*," Microporous and Mesoporous Materials, vol. 124, pp. 210-217 (2009).
Lippens, B.C. et al. "*Studies on Pore Systems in Catalysts V. The t Method*," Journal of Catalysis 4, pp. 319-323 (1965).
Parikh, A.N. et al., "*Non-thermal calcination by ultraviolet irradiation in the synthesis of microporous materials*," Microporous and Mesoporous Materials 76, Elsevier, pp. 17-22 (2004).
Periodic table of the elements, Chemical & Eng. News, p. 27 (Feb. 4, 1985).

*Primary Examiner* — Sharon Pregler
(74) *Attorney, Agent, or Firm* — Darryl M. Tyus

(57) ABSTRACT

A molecular sieve having the structure of COK-5 is produced using, as a structure directing agent, at least one diquaternary ammonium compound selected from the group consisting of 1,4-bis(N-propylpyrrolidinium)butane dications, 1,4-bis(N-butylpyrrolidinium)butane dications and 1,5-bis(N-propylpyrrolidinium)pentane dications.

13 Claims, 14 Drawing Sheets

MOLECULAR SIEVE, COK-5, ITS SYNTHESIS AND USE

CROSS REFERENCE TO RELATED APPLICATIONS

This application is a National Stage Application of International Application No. PCT/US2014/020140, filed Mar. 4, 2014, and claims the benefits of and priorities to U.S. Patent Application Application Ser. No. 61/813940 filed Apr. 19, 2013 and EP Application No. 13172271.2 filed Jun. 17, 2013, the disclosures of which are incorporated herein by reference in their entireties.

FIELD

This invention relates to the molecular sieve, COK-5, its synthesis and its use as an adsorbent and as a catalyst for organic conversion reactions.

BACKGROUND

COK-5 is a molecular sieve zeolite characterized by very thin crystals from about 6 to 20 nm in thickness and a distinctive X-ray diffraction pattern which distinguishes it from other known crystalline materials. COK-5 is a highly versatile catalyst useful in a variety of organic conversion reactions.

An example of thin crystal COK-5 and a method of preparation thereof is disclosed in WO 02/46099-A1, the disclosure of which is incorporated by reference herein in its entirety. WO 02/46099-A1 discloses synthesizing COK-5 with N,N,N,N',N',N'-hexaethylpentane diammonium dibromide (HEPDD) as the structure directing agent:

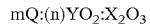

The synthesis further involves a hydrothermal treatment step, which is carried out under conventional zeolite synthesis conditions, and can extend for as long as 7 to 10 days (see WO 02/46099-A1, Examples 1 and 2).

Thus far, HEPDD cations have been identified as the only organic compound known to direct the synthesis of COK-5. Limited by a single identified structure directing agent, the synthesis of COK-5 is a complex process requiring up to 10 days of heating to obtain a final product, as taught by WO 02/46099-A1. Extensive, prolonged heating and the absence of alternative structure directing agents (which could also expand the compositional ranges of the zeolite) lead to various difficulties and increased costs in the production of COK-5, as well as in catalyst manufacture involving COK-5 zeolitic materials.

Therefore, while HEPDD cations can be used as a structure directing agent for the synthesis of COK-5, a need remains for improved structure directing agents, capable of being used in a more simplified synthesis process.

According to the present invention, using one or more of 1,4-bis(N-propylpyrrolidinium)butane dications, 1,4-bis(N-butylpyrrolidinium)butane dications and 1,5-bis(N-propylpyrrolidinium)pentane dications as a structure directing agent, it has now been found that COK-5 can be synthesized by simpler processes and in shorter heating periods than was previously possible using HEPDD as the structure directing agent. Using these new directing agents, COK-5 can be made across a wide range of Si/Al and Si/B atomic ratios under typical OH/SiO$_2$ molar ratios in sodium, potassium, or lithium-containing gels. In addition, it is possible to produce COK-5 with extremely small crystal size resulting in a material having a unique powder X-ray diffraction (XRD) pattern.

SUMMARY

In one aspect, the invention resides in a molecular sieve having the structure of COK-5 and comprising in its pores at least one diquaternary ammonium compound selected from 1,4-bis(N-propylpyrrolidinium)butane dications, 1,4-bis(N-butylpyrrolidinium)butane dications and 1,5-bis(N-propylpyrrolidinium)pentane dications.

In one embodiment, the molecular sieve has a composition comprising the molar relationship:

$$mQ:(n)YO_2:X_2O_3$$

wherein $0<m/n\leq0.2$, n is at least 20, $0<m\leq0.2n$, Q is said at least one diquaternary ammonium compound, X is a trivalent element, such as aluminum or boron, and Y is a tetravalent element, such as silicon.

Conveniently, the molecular sieve comprises crystals having an external surface area of about 100 to about 300 m$^2$/g and a total surface area of about 350 to about 650 m$^2$/g, both as determined by the t-plot method for nitrogen physisorption.

In another aspect, the invention resides in a molecular sieve having the structure of COK-5 and having an X-ray diffraction pattern with a first composite peak with a maximum at 25.0 (±0.30) degrees 2-theta (2θ) which has an intensity above background of Imax$_A$ and which intersects a second composite peak with a maximum at 23.0 (±0.20) degrees 2-theta (2θ) to form a local minimum which has an intensity above background of Imin$_A$, such that the Imin$_A$/Imax$_A$ ratio is >0.7.

In yet another aspect, the invention resides in a molecular sieve having the structure of COK-5 and comprising crystals having an external surface area of at least 100 m$^2$/g as determined by the t-plot method for nitrogen physisorption and having an X-ray diffraction pattern with a single diffuse composite feature in the 2-theta (2θ) range from 21.5 to 25.5 degrees.

In further aspect, the invention resides in a process for producing a molecular sieve having the structure of COK-5, the process comprising:

(i) preparing a synthesis mixture capable of forming said molecular sieve, said mixture comprising a source of an alkali metal (M), a source of an oxide of a tetravalent element (Y), a source of a trivalent element (X), water, and a directing agent (Q) comprising one or more of 1,4-bis(N-propylpyrrolidinium)butane dications, 1,4-bis(N-butylpyrrolidinium)butane dications and 1,5-bis(N-propylpyrrolidinium)pentane dications, and said mixture having a composition, in terms of mole ratios, within the following ranges:

YO$_2$/X$_2$O$_3$ at least 20;
H$_2$O/YO$_2$ about 20 to about 60;
M/YO$_2$ about 0.1 to about 0.5;
OH$^-$/YO$_2$ about 0.2 to about 0.6; and
Q/YO$_2$ about 0.04 to about 0.25;

(ii) heating said mixture under crystallization conditions including a temperature of from about 125° C. to about 200° C. until crystals of said molecular sieve are formed; and (iii) recovering said molecular sieve from step (ii).

In yet further aspect, the invention resides in a process for converting a feedstock comprising an organic compound to a conversion product which comprises contacting said feedstock at organic compound conversion conditions with a catalyst comprising an active form of the molecular sieve described herein.

In still yet further aspect, the invention resides in a 1,4-bis(N-propylpyrrolidinium)butane compound having the following formula:

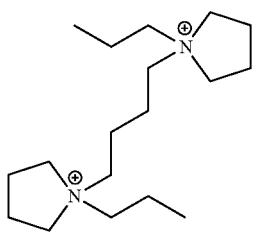

DETAILED DESCRIPTION OF THE EMBODIMENTS

Described herein is a process for the synthesis of the zeolite, COK-5, using as a structure directing agent one or more of the diquaternary ammonium compounds selected from the group consisting of 1,4-bis(N-propylpyrrolidinium)butane dications, 1,4-bis(N-butylpyrrolidinium)butane dications and 1,5-bis(N-propylpyrrolidinium)pentane dications. By using these directing agents, it is found that COK-5, with a broader range of compositions (range of silica to alumina molar ratios and borosilicate compositions) and smaller crystal size, can be obtained as compared to using the HEPDD cations previously employed to produce COK-5.

Also described is a new ultra-small crystal form of COK-5 which exhibits a unique X-ray diffraction pattern.

As conventionally synthesized, zeolite COK-5 is characterized by an X-ray diffraction pattern (XRD) which has, as the only sharp peaks in the degrees 2 theta (2θ) (Cu K-α) region extending from 5 to 25.5 degrees, four sharp peaks at degrees 2 theta (2θ) values of 8.82±0.1, 12.44±0.1, 23.01±0.1 and 25.02±0.1 degrees. Although these are the only sharp peaks in the degrees 2 theta (2θ) (Cu K-α) region extending from 5 to 25.5 degrees 2-theta (2θ), most samples of the zeolite exhibit a number of unresolved broad peaks such that the overall XRD pattern of COK-5 may be summarized as set out in Table 1.

TABLE 1

| Two Theta (2θ), degrees | Intensity | Nature of Peak |
| --- | --- | --- |
| 6 to 8.7 | W/M | Unresolved series of broad peaks |
| 8.82 ± 0.1 | S | Sharp peak |
| 12.44 ± 0.1 | M | Sharp peak |
| 14 to 16 | M | Unresolved series of broad peaks |
| 20.4 to 21.2 | W | Broad peak |
| 23.01 ± 0.1 | VS | Sharp peak |
| 22.5 to 24.5 | M/S | Unresolved series of broad peaks |
| 25.02 ± 0.1 | S | Sharp peak |
| 25.5 to 27 | M | Unresolved series of broad peaks |

Figure 1:
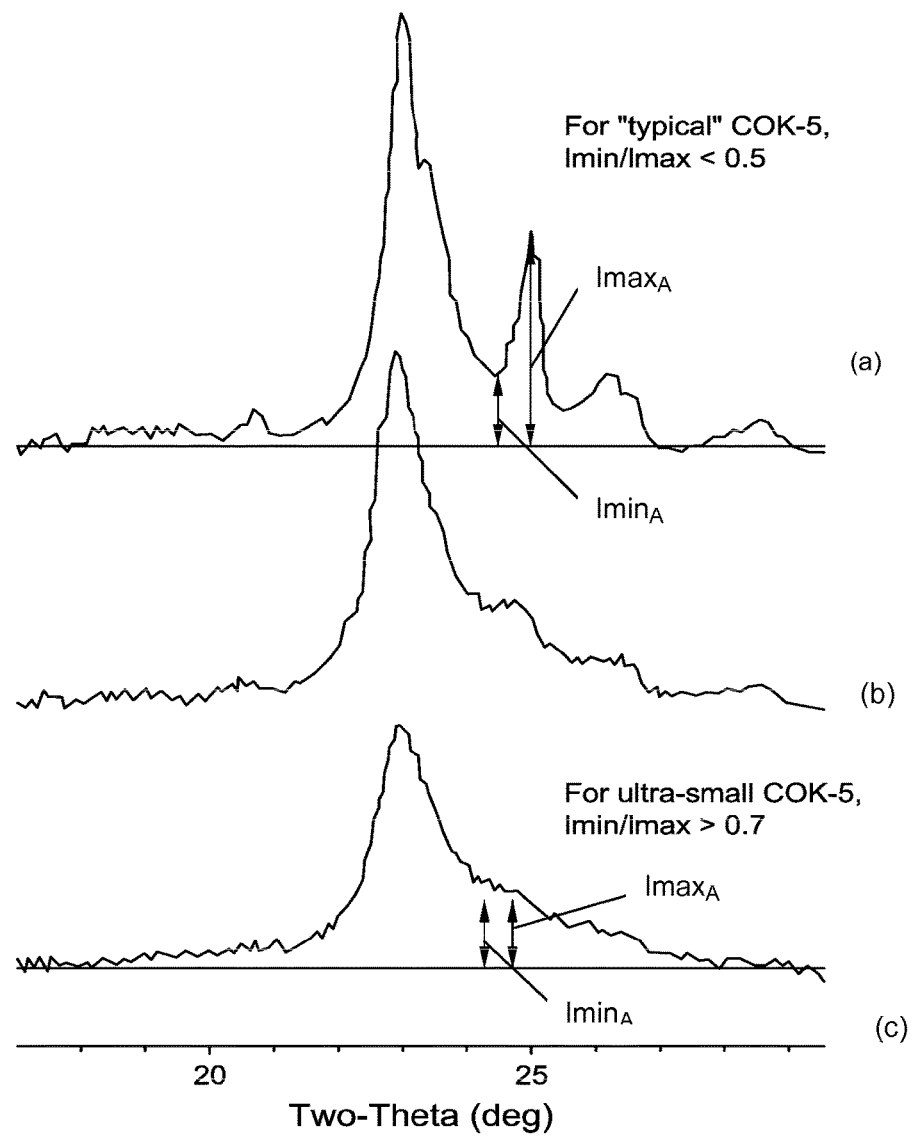
FIG. 1 compares the 20 to 30 degree two theta region of the X-ray diffraction pattern of a conventional COK-5 product with the same region of the X-ray diffraction pattern of a small crystal COK-5 produced according to the present invention.

It is known that certain lines in the X-ray patterns of zeolites tend to broaden as the crystal size of the relevant zeolite decreases so that adjacent lines may begin to overlap and thereby appear as only partially resolved peaks or as unresolved broad peaks. In certain embodiments of the COK-5 described herein, this line broadening results in there being only a diffuse composite peak in the 2-theta (2θ) range from about 21.5 to 25.5 degrees 2-theta (2θ) (CuKα) of the X-ray pattern. In such cases, the maximum of the composite peak near 25.0 (±0.1) degrees 2-theta (2θ) either appears as a shoulder or forms part of a large diffuse composite feature with the peak with maximum near 23.0 (±0.1) degrees 2-theta (2θ). In a powder XRD pattern of a typical (larger crystallite) COK-5 sample, the composite peak with a maximum near 23.0 degrees 2-theta (2θ) and the composite peak near 25.0 degrees 2-theta (2θ) will intersect to form a clearly visible local minimum [see FIG. 1(a)]. In these typical preparations, the ratio of the relative background-subtracted intensity of this local minimum to the relative background-subtracted intensity of the composite peak near 25.0 degrees 2-theta (2θ) will be less than 0.5 in both the as-made and calcined forms of the zeolite. In one embodiment of the small crystal preparations described herein, the local minimum may be clearly discerned from the composite peak near 25.0 degrees 2-theta (2θ) but this ratio will be greater than 0.70. In another embodiment, the crystals become so small and the peaks are so severely broadened that the peak maximum near 25.0 degrees 2-theta (2θ) either appears as an inflection point of the large diffuse composite peak with a maximum near 23.0 (±0.20) degrees 2-theta (2θ) or no local maximum or inflection point is discerned for the composite peak near 25.0 (±0.30) degrees 2-theta (2θ) [see FIG. 1(b) and FIG. 1(c)].

It will be appreciated that, with the ultra-small crystal embodiments described above, X-ray diffraction alone may not be sufficient to identify the material as having the COK-5 structure, in which case other analytical methods, such as high resolution transmission electron microscopy and electron diffraction, may be necessary to confirm the identity of the material as COK-5.

The X-ray diffraction data reported herein were collected with a Panalytical X'Pert Pro diffraction system with an Xcelerator multichannel detector, equipped with a germanium solid state detector, using copper K-alpha radiation. The diffraction data were recorded by step-scanning at 0.02 degrees of two-theta, where theta is the Bragg angle, and an effective counting time of 2 seconds for each step. The interplanar spacings, d-spacings, were calculated in Angstrom units, and the relative intensities of the lines, $I/I_o$ is one-hundredth of the absolute intensity of the strongest line, above background. The intensities are uncorrected for Lorentz and polarization effects. The relative intensities are given in terms of the symbols vs=very strong (75-100), s=strong (50-74), m=medium (25-49) and w=weak (0-24).

In its as-synthesized form, the COK-5 described herein has a composition comprising the molar relationship:

mQ:(n)YO$_2$:X$_2$O$_3$, wherein 0<m/n≤0.2, n is at least 20, 0<m≤0.2n, Q is said at least one diquaternary ammonium compound selected from 1,4-bis(N-propylpyrrolidinium)butane dications, 1,4-bis(N-butylpyrrolidinium)butane dications and 1,5-bis(N-propylpyrrolidinium)pentane dications, X is a trivalent element, such as boron or aluminum, and Y is a tetravalent element, such as silicon.

The COK-5 described herein is produced from a synthesis mixture comprising a source of an alkali metal (M), a source of an oxide of a tetravalent element (Y), a source of a trivalent element (X), water, and a directing agent (Q) comprising one or more of 1,4-bis(N-propylpyrrolidinium) butane dications, 1,4-bis(N-butylpyrrolidinium)butane dications and 1,5-bis(N-propylpyrrolidinium)pentane dications, wherein the mixture has a composition, in terms of mole ratios, within the following ranges:

| Reactants | Useful | Preferred |
|---|---|---|
| YO$_2$/X$_2$O$_3$ | 20 to 200 | 24 to 100 |
| H$_2$O/YO$_2$ | 15 to 60 | 20 to 45 |
| OH$^-$/YO$_2$ | 0.2 to 0.6 | 0.3 to 0.5 |
| Q/YO$_2$ | 0.04 to 0.5 | 0.05 to 0.2 |

The alkali metal (M) is generally potassium, sodium or lithium and a suitable source of the alkali metal is the hydroxide.

Suitable sources of the trivalent element X depend on the element X selected but, in one preferred embodiment, in which the element X is aluminum or boron, suitable sources of aluminum include hydrated alumina and fumed alumina and water-soluble aluminum salts, such as aluminum nitrate. Suitable sources of boron include boric acid and water-soluble borate salts, such as sodium borate.

Suitable sources of the tetravalent element Y depend on the element Y selected but, in one preferred embodiment, in which Y is silicon, include colloidal suspensions of silica, precipitated silica, alkali metal silicates, tetraalkyl orthosilicates, and fumed silicas.

Combined sources of two or more of the components M, X and Y can also be used as sodium aluminate and metakaolin.

Suitable sources of the directing agent Q include the hydroxides and/or salts of the relevant quaternary ammonium compounds. 1,4-bis(N-propylpyrrolidinium)butane and 1,5-bis(N-propylpyrrolidinium)pentane compounds can be readily synthesized by the reaction of N-propylpyrrolidine with 1,4-dibromobutane and 1,5-dibromopentane, respectively. Similarly, 1,4-bis(N-butylpyrrolidinium)butane compounds can be readily synthesized by the reaction of N-butylpyrrolidine with 1,4-dibromobutane. N-propylpyrrolidine and N-butylpyrrolidine are known materials but can be synthesized by reaction of pyrrolidine with 1-iodopropane and 1-iodobutane, respectively, or by reductive amination of propionaldehyde or butyraldehyde with pyrrolidine.

Crystallization of COK-5 from the above synthesis mixture can be carried out at either static or stirred conditions in a suitable reactor vessel, such as for example, polypropylene jars or teflon lined or stainless steel autoclaves, at a temperature of about 125° C. to about 200° C. for a time sufficient for crystallization to occur at the temperature used, e.g., at least 1 day, such as from about 1 to about 21 days. Thereafter, the crystals are separated from the liquid and recovered.

The synthesis may be aided by seeds from a previous synthesis of COK-5, with the seeds suitably being present in an amount of from about 0.01 ppm by weight to about 10,000 ppm by weight, such as from about 100 ppm by weight to about 5,000 ppm by weight of the synthesis mixture.

To the extent desired and depending on the X$_2$O$_3$/YO$_2$ molar ratio of the material, any alkali or alkaline earth metal cations in the as-synthesized COK-5 can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The as-synthesized COK-5 may also be subjected to treatment to remove part or all of the organic directing agent Q used in its synthesis. This is conveniently effected by thermal treatment in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. Alternatively, the organic directing agent Q can be removed by treatment with ozone (see, e.g., Parikh et al., Microporous and Mesoporous Materials 76 (2004) pp. 17-22).

The COK-5 molecular sieve produced by the present process forms as flake-like crystals. Depending on their size, the crystals may have an external surface area of at least 100 m$^2$/g, such as about 100 to about 300 m$^2$/g and a total surface area of at least 350 m$^2$/g, such as about 350 to about 650 m$^2$/g. All surface area values given herein are determined from nitrogen physisorption data using the t-plot method. Details of this method can be found in Lippens, B. C. and deBoer, J. H., "Studies on pore systems in catalysts: V. The t method", J. Catal., 4, 319 (1965), the entire contents of which are incorporated herein by reference.

The COK-5 produced by the present process, if required after cation exchange and/or calcining, has utility as a catalyst or catalyst precursor and as a separation and absorption medium. The material is especially useful in numerous hydrocarbon conversions, separations and adsorptions. It may be used alone, or in admixture with other molecular sieves, in particulate form, supported or unsupported, or in the form of a supported layer. Hydrocarbon conversions include, for example, cracking, reforming, hydrofining, aromatization, oligomerization (e.g., di- and trimerization, especially of olefins having 3 to 6 carbon atoms, more particularly butene trimerization), isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons.

The invention will now be more particularly described with reference to the following non-limiting Examples and the accompanying drawings.

EXAMPLE 1

COK-5 synthesis with 1,4-bis(N-butylpyrrolidinium)butane cations 1,4-bis(N-butylpyrrolidinium)butane cations were prepared by adding 50 g N-butylpyrrolidine (0.39 mol, Aldrich) to 170 mL acetonitrile in a 3-necked round bottom flask. Next 36.7 g 1,4-dibromobutane (0.17 mol) was added dropwise with stirring. The reaction was then refluxed for 5 hours. The precipitated solids were then filtered with a Buchner funnel, washed with acetone, washed with ether, and then allowed to dry. $^1$H NMR showed the compound to be pure. The dibromide salt was then ion-exchanged into the hydroxide form by dissolving in water and passing it through a column of Dowex LC NG hydroxide exchange resin. The concentration of the aqueous solution was determined by titration with a standard solution of 0.1 N HCl.

A gel was prepared by mixing 3.45 g of the 1,4-bis(N-butylpyrrolidinium)butane diquat solution ([OH]=0.87 mmol/g) with 2.63 g 1 N KOH and 0.94 g deionized water inside a Teflon liner for a 23-mL steel Parr autoclave. 0.085 g fumed alumina was then mixed with the solution to create a uniform suspension. 2.25 g Ludox AS-40 was then mixed with the suspension to form a gel having the following composition: Si/Al=9, the total OH/SiO$_2$=0.375, and KOH/SiO$_2$=0.175.

Figure 2:
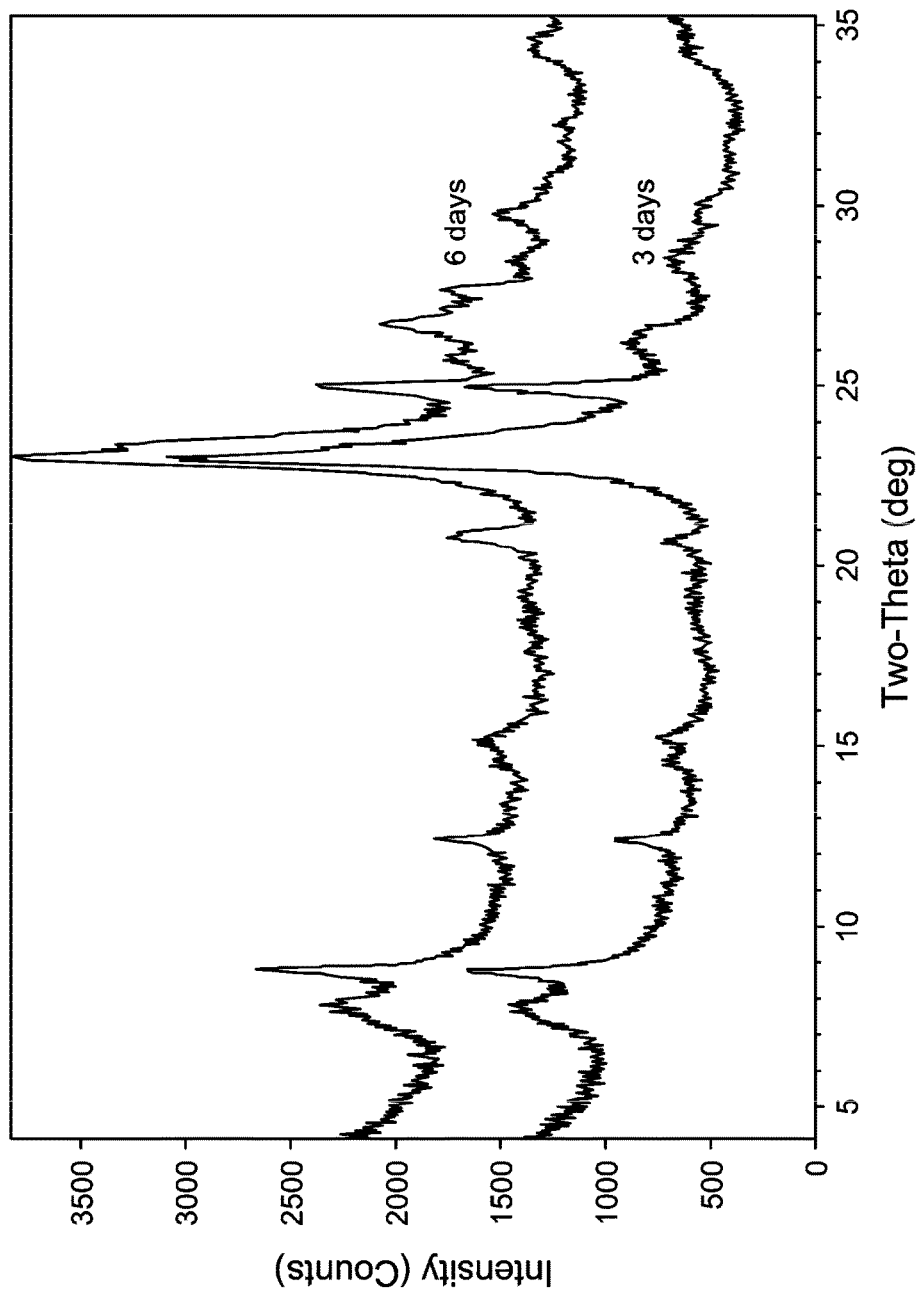
FIG. 2 shows the X-ray diffraction patterns of the as-synthesized products of Example 1 after crystallization for 3 days and 6 days.

The liner was then capped, sealed inside a 23-mL autoclave, and heated at 160° C. under tumbling conditions (~50 rpm). The solids were then isolated by filtering through a Buchner funnel, washing with deionized water, and drying in a vacuum oven at 60° C. FIG. 2 shows the powder diffraction patterns of samples obtained after 3 and 6 days of heating. The powder diffraction pattern of the 3-day timepoint matches that of the COK-5. After a few days of additional heating, there are additional peaks around 26-28 degrees 2 theta (2θ) that are due to sanidine, a dense phase potassium aluminosilicate.

Similar preparations using alumina trihydrate as the Al source were also found to produce COK-5.

EXAMPLE 2

COK-5 synthesis with 1,4-bis(N-butylpyrrolidinium)butane cations

Figure 3:
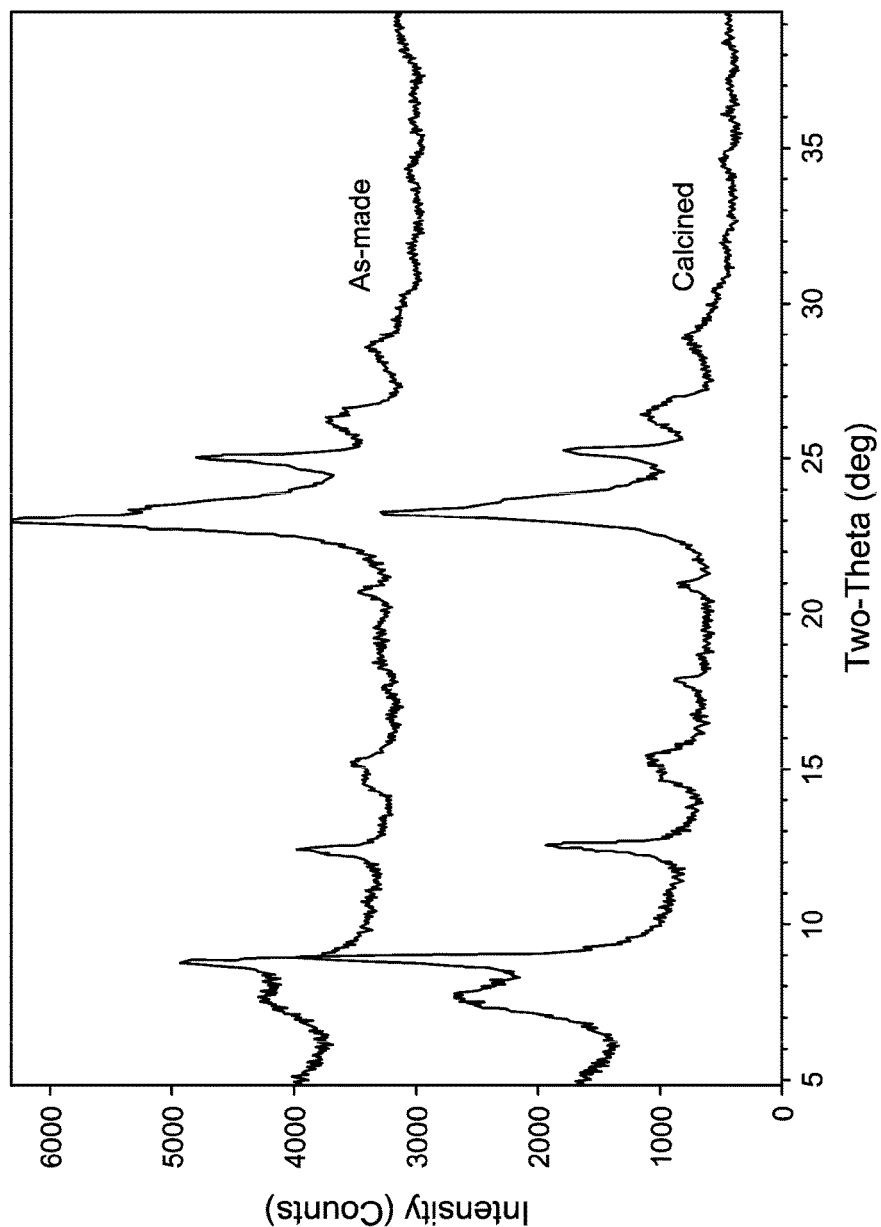
FIG. 3 shows the X-ray diffraction patterns of the as-synthesized (as-made) and as-calcined products of Example 2.
Figure 4:
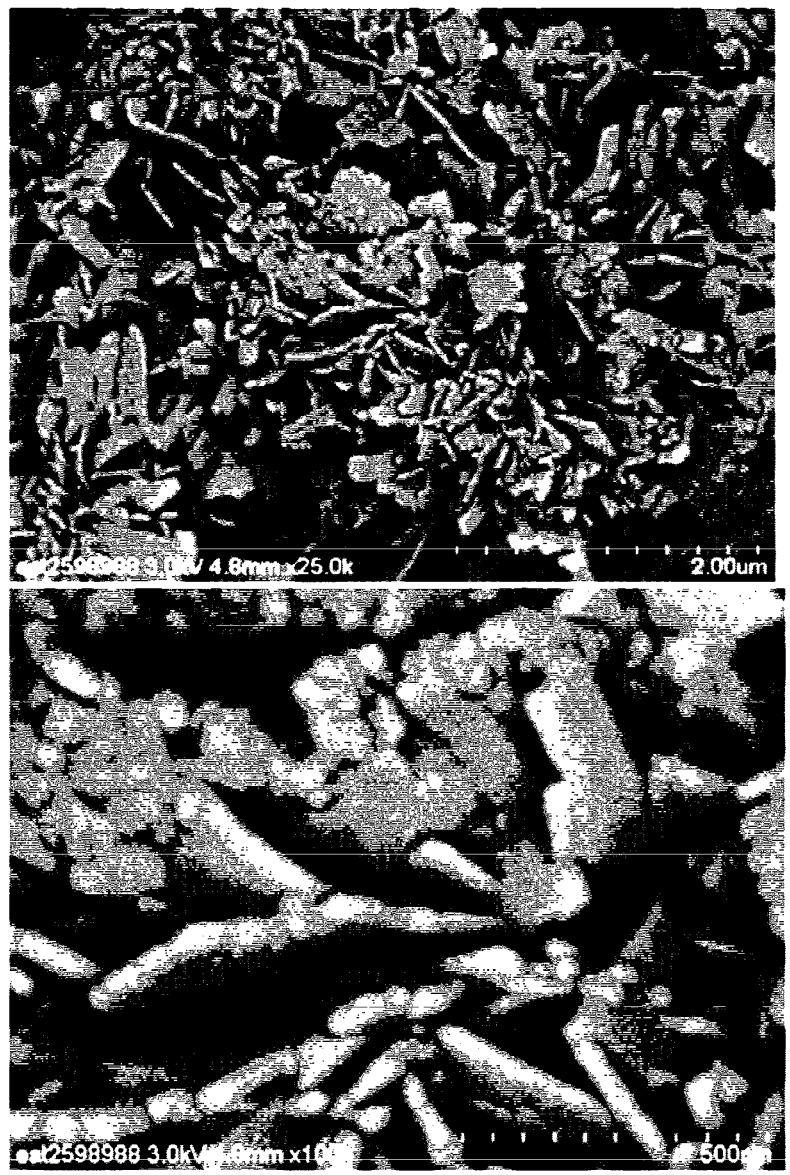
FIG. 4 shows scanning electron micrograph (SEM) images of the as-synthesized product of Example 2.

Example 1 was repeated with less (⅔) aluminum so that the gel Si/Al=13.5. After 3 days, a product with a clean diffraction pattern was obtained. X-ray diffraction patterns for the as-synthesized and as-calcined products are shown in FIG. 3, while FIG. 4 shows SEM images of the as-synthesized product. The zeolite was heated inside a muffle furnace from ambient temperature to 400° C. at 4° C./min under a nitrogen atmosphere, then heated to 600° C. at 4° C./min in air, and maintained at 600° C. in air for 2 hours. After calcination, the sample was ammonium-exchanged in a solution created by dissolving an equal mass ammonium nitrate (to that of the zeolite) in a 10-fold mass of the zeolite. The zeolite/ammonium nitrate suspension was heated overnight in a steambox at 98° C. The zeolite was then isolated by filtration, washed thoroughly with deionized water, and allowed to dry overnight in a vacuum oven at 60° C. The zeolite was then calcined to 500° C. to convert it to the acidic form. The surface area of the sample was then measured using nitrogen physisorption and the data were analyzed with the t-plot method. The determined internal micropore surface area is 270 m$^2$/g and the external surface area is 196 m$^2$/g (total surface area of 466 m$^2$/g).

EXAMPLE 3

COK-5 synthesis with 1,4-bis(N-propylpyrrolidinium)butane cations

N-propylpyrrolidine was prepared by adding 75.0 g pyrrolidine (1.06 mol) to 300 mL methanol in a round-bottom flask. 206.5 g 1-iodopropane (1.21 mol) was then added dropwise with stirring. The mixture was then refluxed for 1 hour. The methanol was then removed under vacuum in a rotary evaporator, and then 100 mL deionized water was added to the liquid residue. The aqueous mixture was then extracted with ether to remove unreacted 1-iodopropane. 77.30 g KOH was then dissolved in 100 mL deionized water; this basic solution was then added to the aqueous fraction (the reason for this step is that most of the product is in the form a hydrohalide salt; the base neutralizes the HI component and frees the amine so that it can be more easily isolated from the aqueous fraction). The mixture was then extracted with ether, and the ethyl ether was removed under vacuum by rotary evaporation to yield 97% N-propylpyrrolidine (the other 3% was ether as inferred from $^1$H NMR).

The diquat was then formed by adding 25.0 g of the 97% N-propylpyrrolidine (0.21 mol) to 60 mL acetonitrile inside a Teflon liner for a 125-mL steel Parr autoclave. Next 21.0 g 1,4-dibromobutane (0.097 mol) was added to the mixture. The 125-mL Teflon liner was capped, sealed inside the Parr autoclave, and then heated at 80° C. for 4 days. The precipitated solids were then filtered, washed with acetone, washed with ethyl ether, and then allowed to dry. The total mass of clean product (by $^1$H and $^{13}$C NMR) was 42.6 g (97% yield). The dibromide salt was then ion-exchanged into the hydroxide form by dissolving in water and passing it through a column of Dowex LC NG hydroxide exchange resin. The concentration of the aqueous solution was determined by titration with a standard solution of 0.1 N HCl.

The resultant diquat solution was used in a plurality of parallel small scale (1 ml) synthesis reactions using gels having compositions with Si/Al,B=100 to 20 under typical OH/SiO$_2$ molar ratios and containing sodium, potassium, or lithium cations. Aluminum nitrate was used as the Al source and boric acid was used as the B source. Details of the synthesis reactions are given in Table 2, where Q refers to the 1,4-bis(N-propylpyrrolidinium)butane diquat and T refers to the T-atom, and where the ratios in column 2 are expressed as atomic ratios and the ratios in columns 3, 4 and 5 are expressed as molar ratios.

TABLE 2

| Run | T$^{3+}$, Si/T$^{3+}$ | M, MOH/SiO$_2$ | Q/Si | Free OH/SiO$_2$* | Temp ° C., Time |
|---|---|---|---|---|---|
| A | Al, 40 | Na, 0.30 | 0.15 | 0.30 | 160° C., 4 days |
| B | Al, 100 | Na, 0.30 | 0.10 | 0.20 | 160° C., 4 days |
| C | B, 100 | K, 0.15 | 0.15 | 0.30 | 160° C., 7 days |
| D | Al, 40 | Na, 0.30 | 0.19 | 0.60 | 160° C., 7 days |
| E | Al, 40 | Na = Li, 0.30 | 0.19 | 0.60 | 160° C., 7 days |
| F | Al, 20 | K, 0.30 | 0.23 | 0.60 | 160° C., 7 days |
| G | Al, 20 | Na = Li, 0.30 | 0.23 | 0.60 | 160° C., 7 days |
| H | B, 40 | Li, 0.30 | 0.15 | 0.60 | 160° C., 4 days |
| I | Al, 40 | Na, 0.15 | 0.15 | 0.30 | 160° C., 7 days |
| J | Al, 40 | Na, 0.30 | 0.15 | 0.30 | 160° C., 7 days |
| K | B, 20 | Na, 0.30 | 0.15 | 0.30 | 160° C., 7 days |
| L | Al, 40 | Na, 0.30 | 0.15 | 0.40 | 160° C., 7 days |

*Free OH/SiO$_2$ accounts for neutralization of hydroxide by aluminum sources and by addition of HCl to bring the concentration to the specified OH/SiO$_2$ molar ratio.

Each of the synthesis reactions produced COK-5, in some cases in times as short as 4 days. In fact, the 1,4-bis(N-propylpyrrolidinium)butane diquat was found to be remarkably selective for the synthesis of COK-5.

EXAMPLE 4

Figure 5:
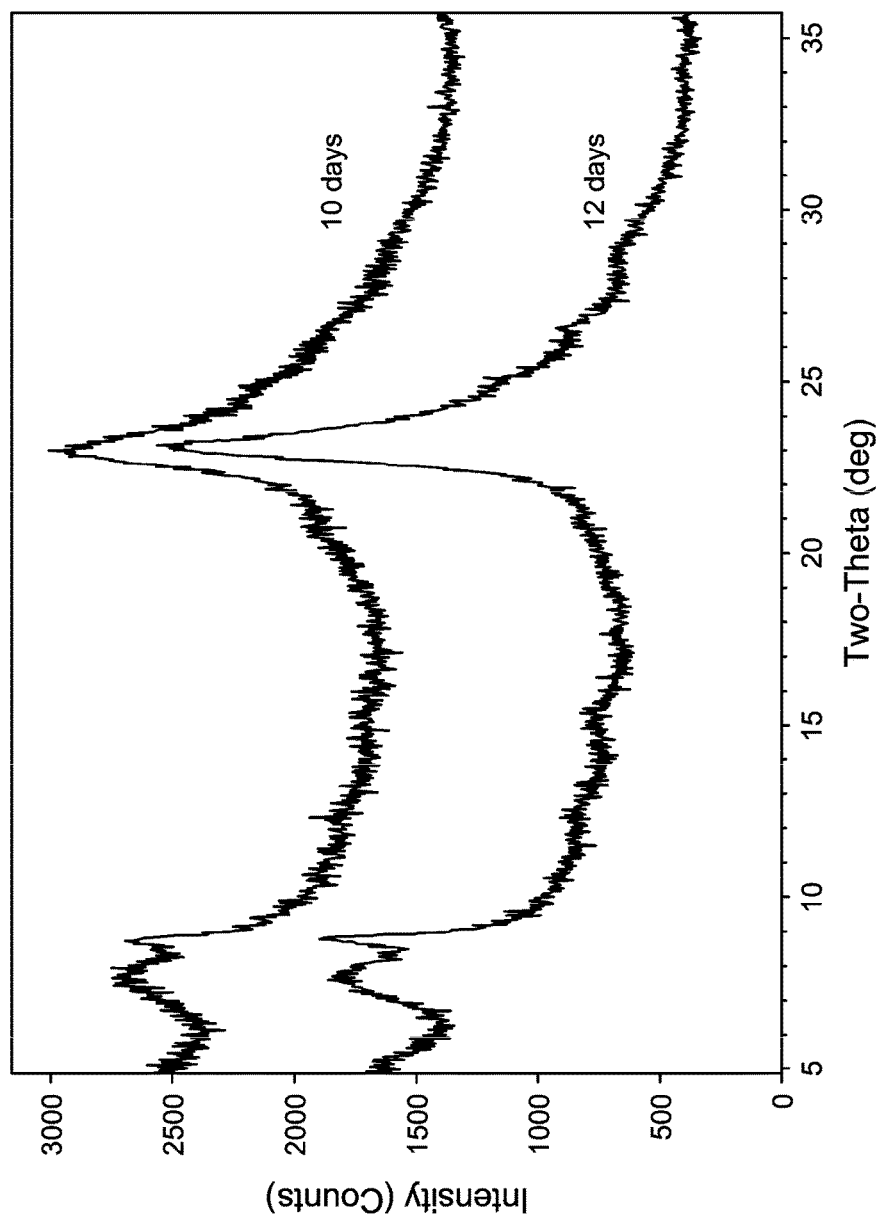
FIG. 5 shows the X-ray diffraction patterns of the as-synthesized products of Example 4 after crystallization for 10 days and 12 days.

COK-5 synthesis with
1,4-bis(N-butylpyrrolidinium)butane cations 3.45 g of an aqueous solution of 1,4-(N-butylpyrrolidinium)butane hydroxide ([OH]=0.87 mmol/g) was mixed with 2.63 g 1 N KOH and 0.94 g deionized water inside a 23-mL Teflon insert for a steel Parr autoclave. Next 0.06 g fumed alumina (Cabot) was added to the solution. The liner was then capped and sealed within a steel Parr autoclave and heated at 160° C. under tumbling conditions for 1 hour. The autoclave was then removed and allowed to cool to ambient temperature. The autoclave was then opened and 2.25 g Ludox AS-40 was added to the mixture. The Teflon liner was then capped and sealed the steel autoclave. The autoclave was then placed in an oven at 160° C. under tumbling conditions (50 rpm). FIG. 5 shows the powder XRD of the solid products after 10 and 12 days of heating. ICP of the 10-day product showed the material to have a Si/Al ratio of 12.3. $^{27}$Al NMR of the 12-day product shows that the aluminum in the final product is tetrahedral.

EXAMPLE 5

Figure 6:
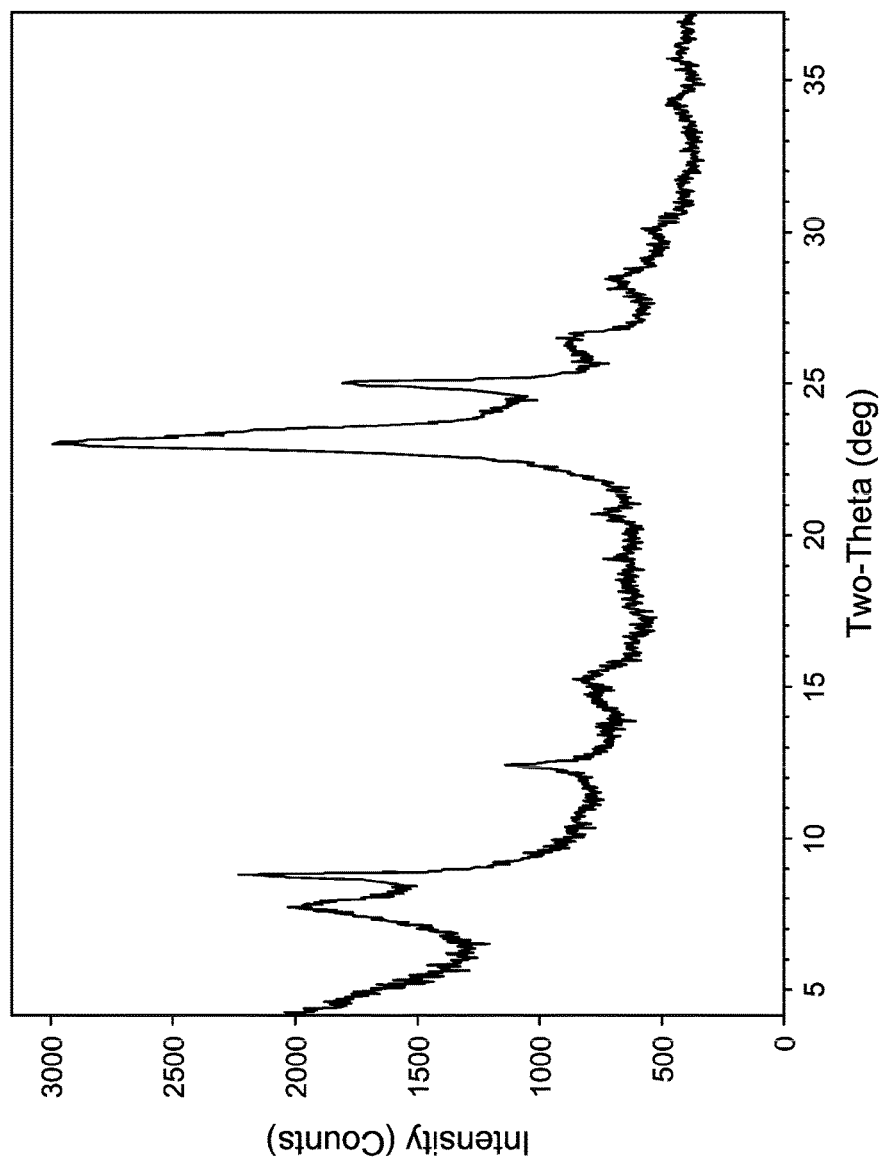
FIG. 6 shows the X-ray diffraction patterns of the as-synthesized product of Example 5.

COK-5 synthesis with
1,4-bis(N-butylpyrrolidinium)butane cations 3.45 g of an aqueous solution of 1,4-(N-butylpyrrolidinium)butane hydroxide ([OH]=0.87 mmol/g) was mixed with 2.63 g 1 N KOH and 2.93 g deionized water inside a 23-mL Teflon insert for a steel Parr autoclave. Next 2.08 g Ludox AS-40 (40% silica) and 0.13 g metakaolin were added to the solution. The Teflon liner was then capped and sealed within a 23-mL Parr steel autoclave. The autoclave was then placed in a spit within an oven at 160° C. under tumbling conditions (50 rpm) for 3 days. Powder XRD (FIG. 6) of the resulting solid product showed it to be pure COK-5.

EXAMPLE 6

COK-5 synthesis with
1,4-bis(N-butylpyrrolidinium)butane cations

Figure 7:
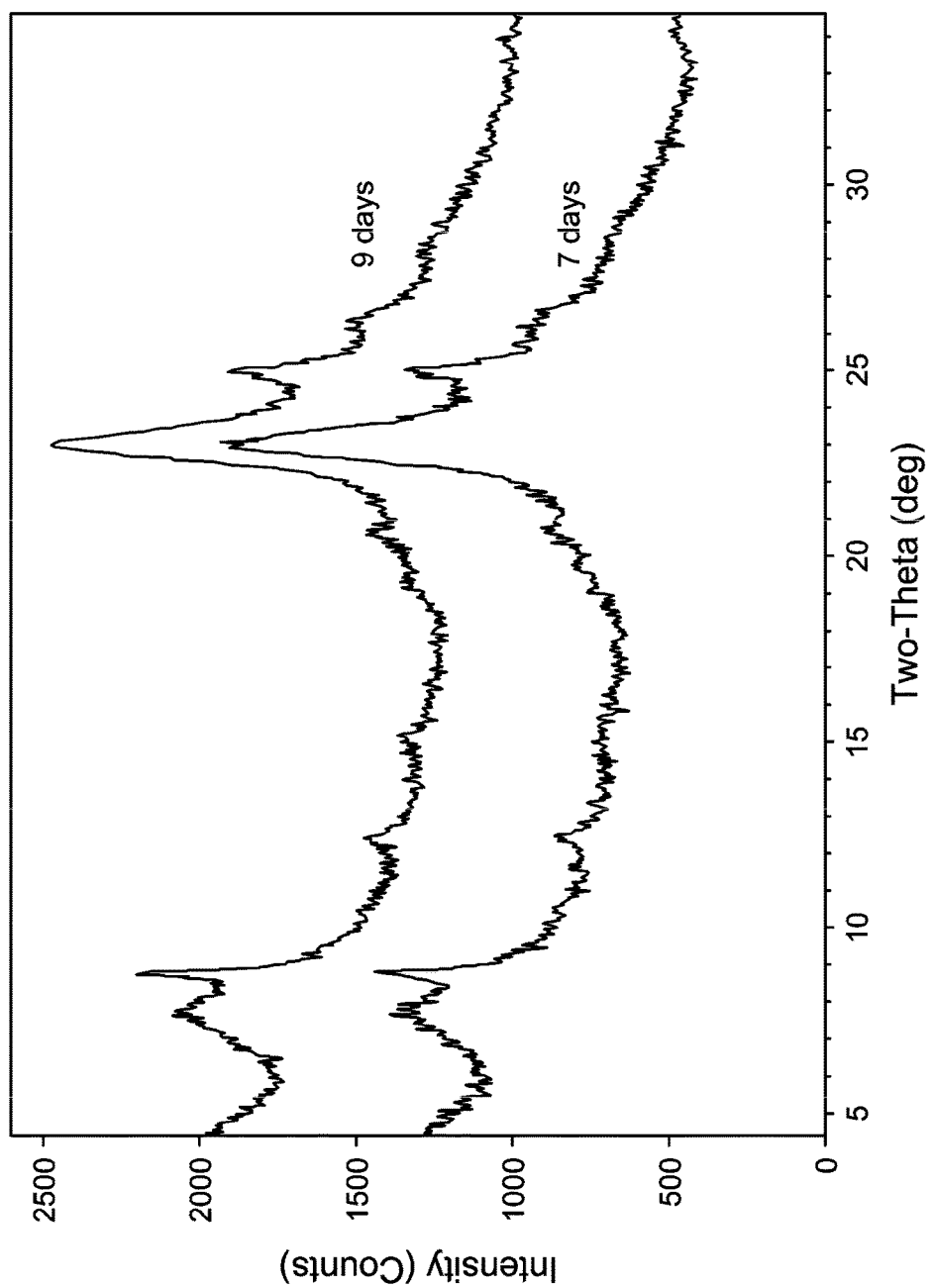
FIG. 7 shows the X-ray diffraction patterns of the as-synthesized products of Example 6 after crystallization for 7 days and 9 days.
Figure 8:
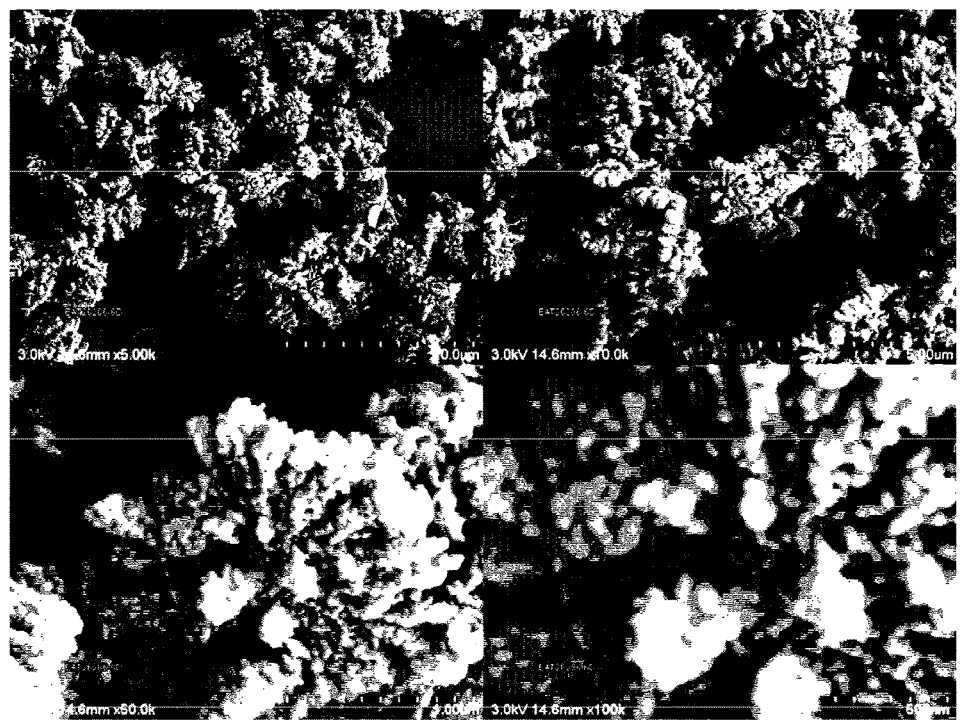
FIG. 8 shows scanning electron micrograph (SEM) images of the as-synthesized product of Example 6 after crystallization for 9 days.

Example 5 was repeated except the synthesis was performed at 140° C. and the reaction was sampled after 7 and 9 days. FIG. 7 provides the powder XRD patterns of the COK-5 products and shows some peak broadening as compared with the product of Example 5. FIG. 8 shows SEM images of the 9-day product.

EXAMPLE 7

Figure 9:
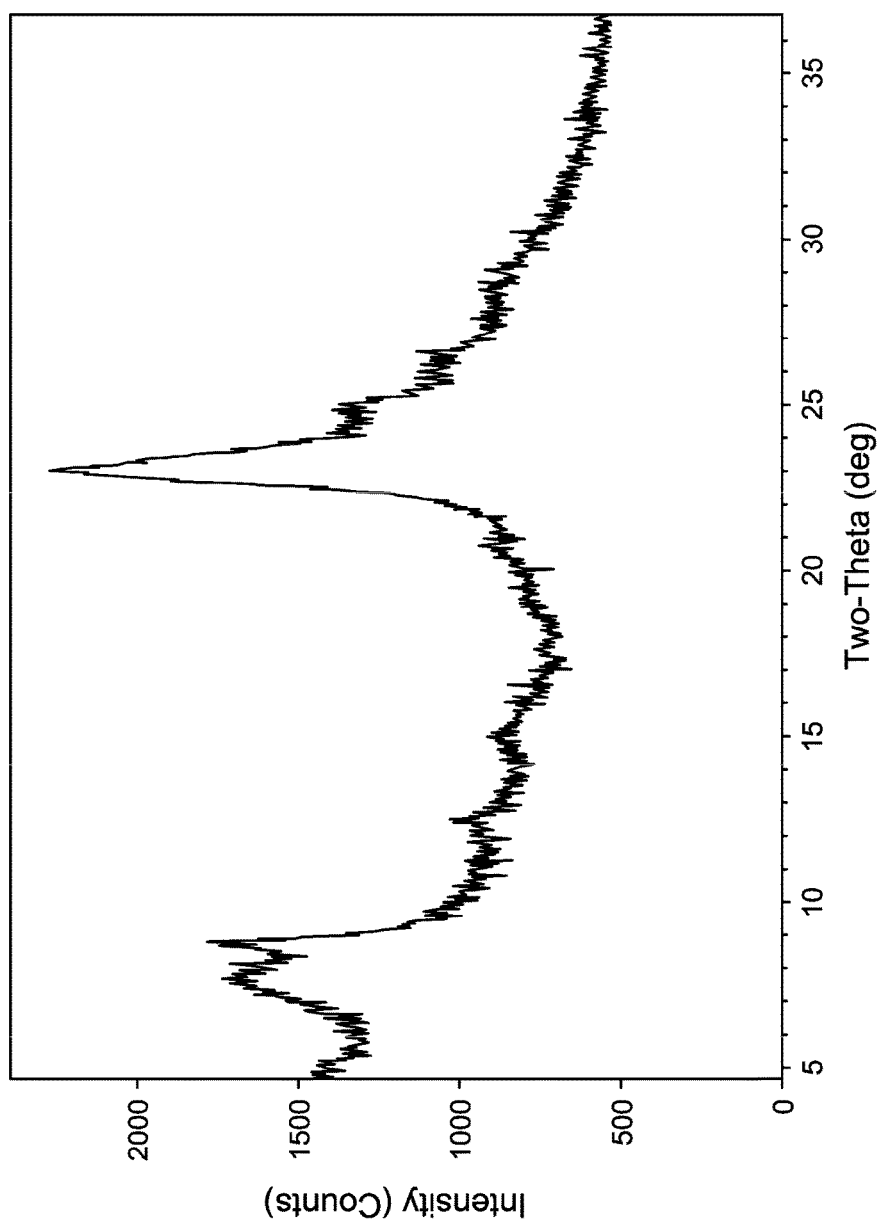
FIG. 9 shows the X-ray diffraction patterns of the as-synthesized product of Example 7.
Figure 10:
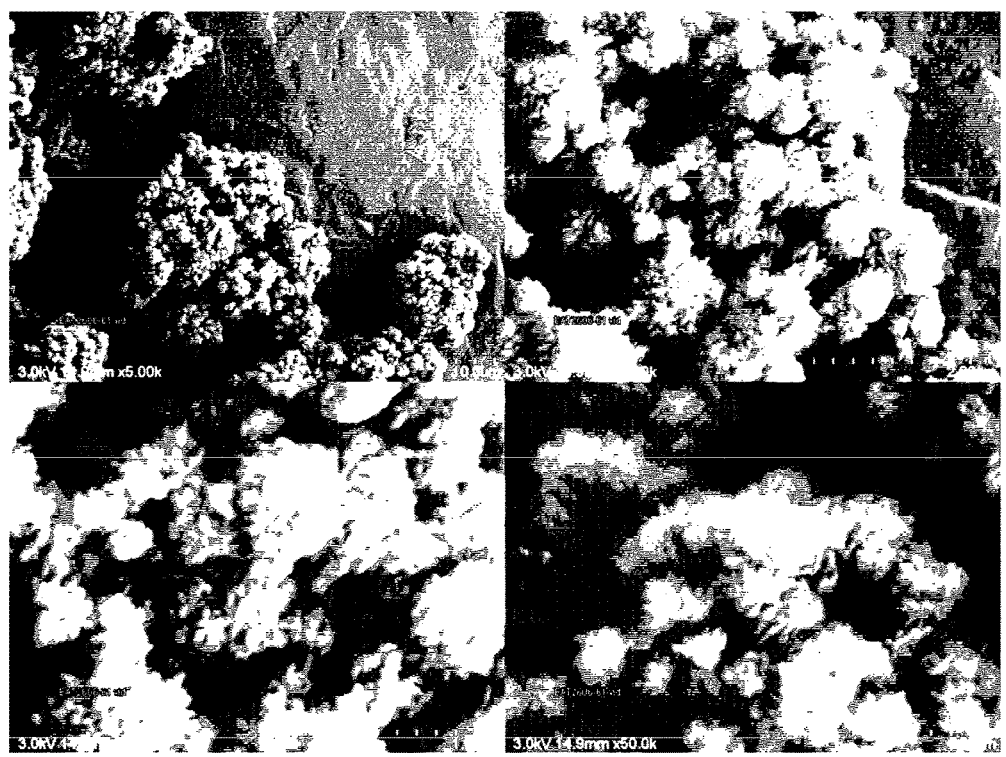
FIG. 10 shows scanning electron micrograph (SEM) images of the as-synthesized product of Example 7.

COK-5 synthesis with
1,4-bis(N-butylpyrrolidinium)butane cations 31.80 g of an aqueous solution of 1,4-(N-butylpyrrolidinium)butane hydroxide ([OH]=0.86 mmol/g) was mixed with 23.96 g 1 N KOH and 8.2 g deionized water inside an 125-mL Teflon insert for a steel Parr autoclave. Next 0.55 g fumed alumina (Cabot) was added to the solution. The liner was then capped and sealed within a steel Parr autoclave and heated at 150° C. under tumbling conditions for 1 hour. The autoclave was then removed and allowed to cool to ambient temperature. The autoclave was then opened and 20.5 g Ludox AS-40 was added to the mixture. The Teflon liner was then capped and sealed within the steel autoclave. The autoclave was then placed in a spit within an oven at 150° C. under tumbling conditions (30 rpm) for 9 days. FIG. 9 shows the powder XRD of the COK-5 product and FIG. 10 shows the corresponding SEM images.

EXAMPLE 8

Figure 11:
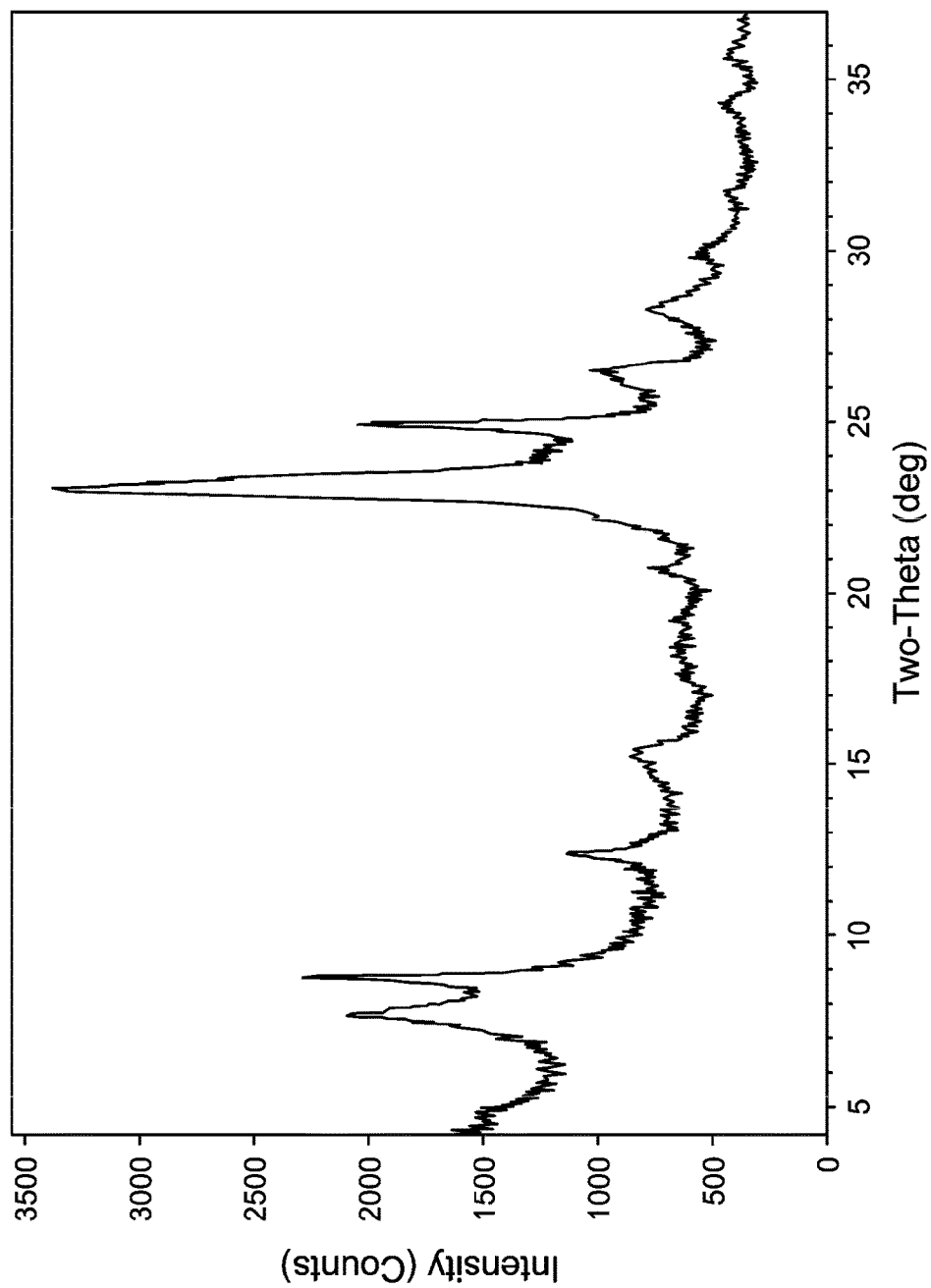
FIG. 11 shows the X-ray diffraction patterns of the as-synthesized product of Example 8.
Figure 12:
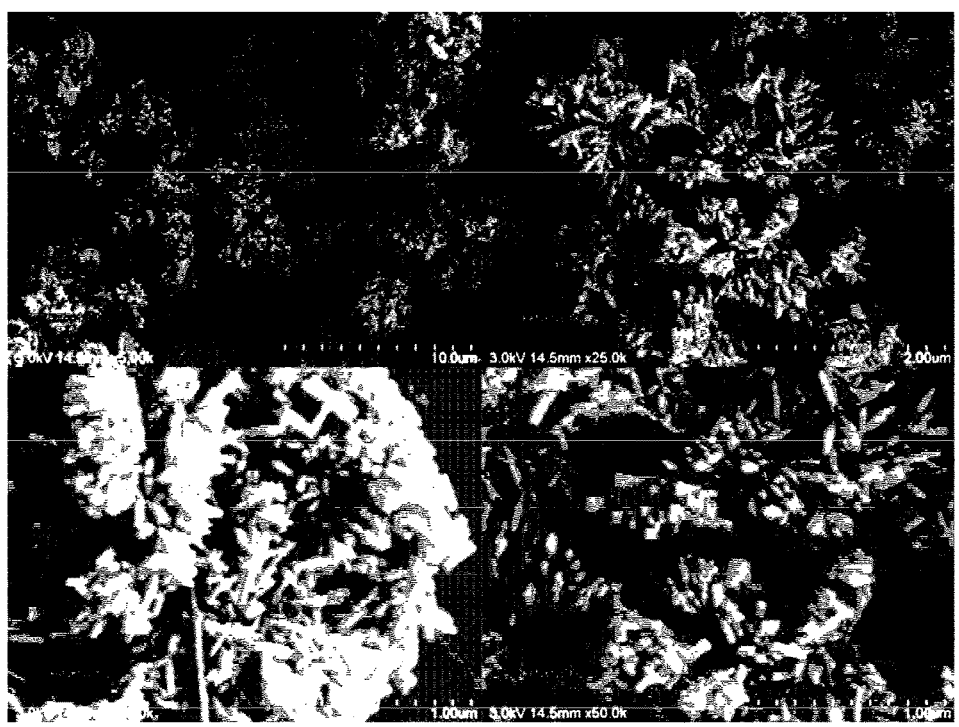
FIG. 12 shows scanning electron micrograph (SEM) images of the as-synthesized product of Example 8.

COK-5 synthesis with
1,4-bis(N-butylpyrrolidinium)butane cations 23.96 g 1 N KOH and 8.57 g deionized water were mixed inside an 125-mL Teflon insert for a steel Parr autoclave. Next 0.55 g fumed alumina (Cabot) was added to the solution. The liner was then capped and sealed within a steel Parr autoclave and heated at 160° C. under tumbling conditions for 30 minutes. The autoclave was then removed and allowed to cool to ambient temperature. The autoclave was then opened and 31.43 g of an aqueous solution of 1,4-(N-butylpyrrolidinium)butane hydroxide ([OH]=0.87 mmol/g) was added to the suspension. The Teflon liner was then capped and sealed inside the autoclave. The autoclave was then placed in an oven at 160° C. under tumbling conditions for 40 minutes. The autoclave was then removed and allowed to cool to ambient temperature. The autoclave was opened and 20.5 g Ludox AS-40 was added to the mixture. The Teflon liner was then capped and sealed in the steel autoclave. The autoclave was then placed in a spit within an oven at 160° C. under tumbling conditions (30 rpm) for 7 days. FIG. 11 shows the powder XRD of the COK-5 product and FIG. 12 shows the corresponding SEM images.

EXAMPLE 9

COK-5 synthesis with
1,4-bis(N-butylpyrrolidinium)butane cations

Figure 13:
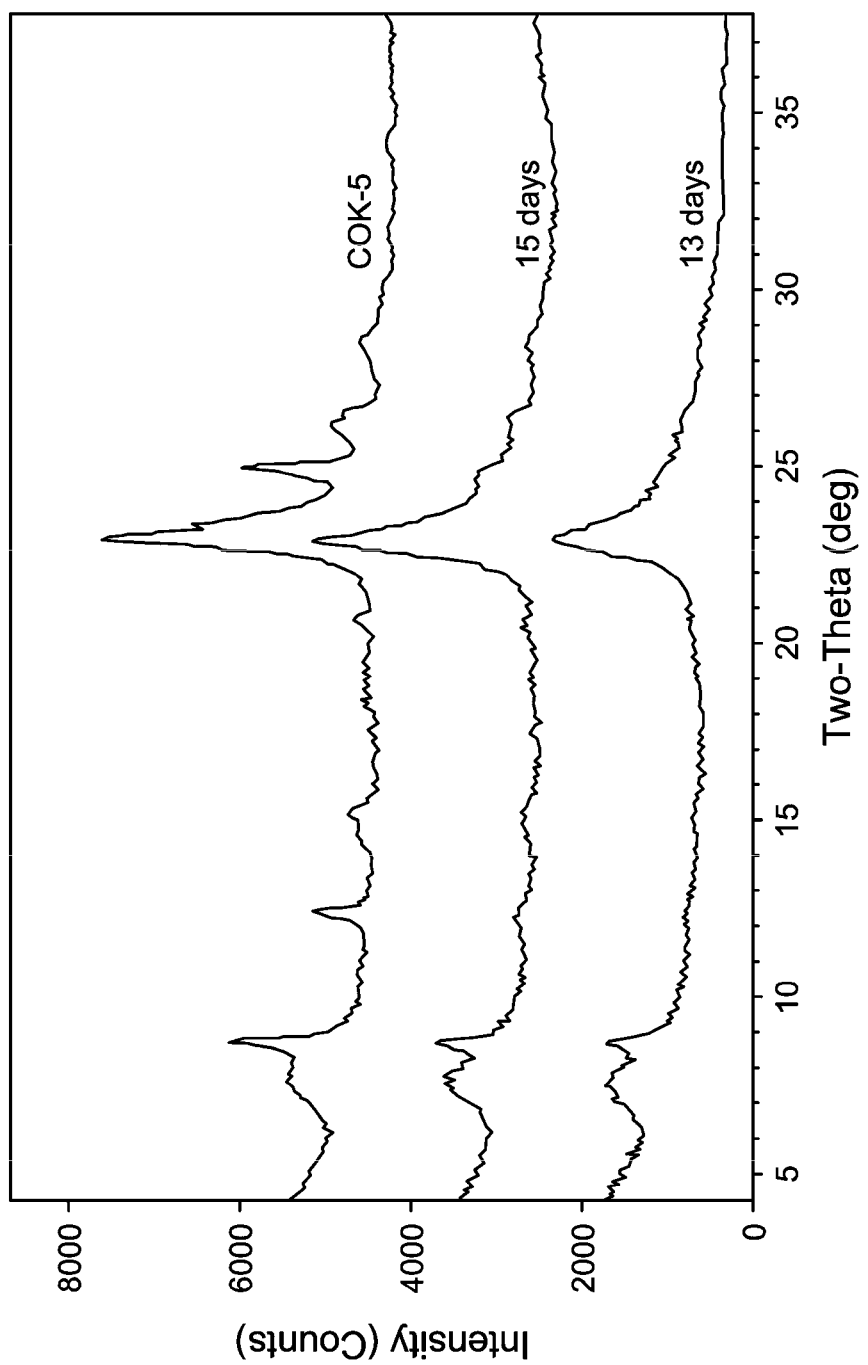
FIG. 13 compares the X-ray diffraction patterns of the as-synthesized products of Example 9 after crystallization for 13 days and 15 days with that of conventional COK-5.
Figure 14:
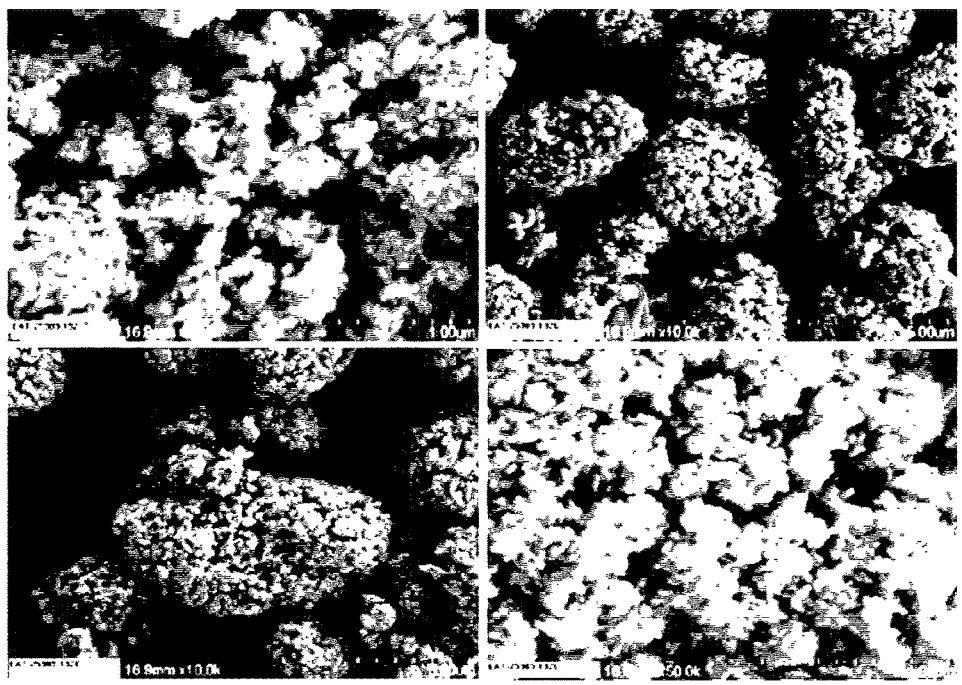
FIG. 14 shows SEM images of the 13-day product of Example 9.
Figure 15:
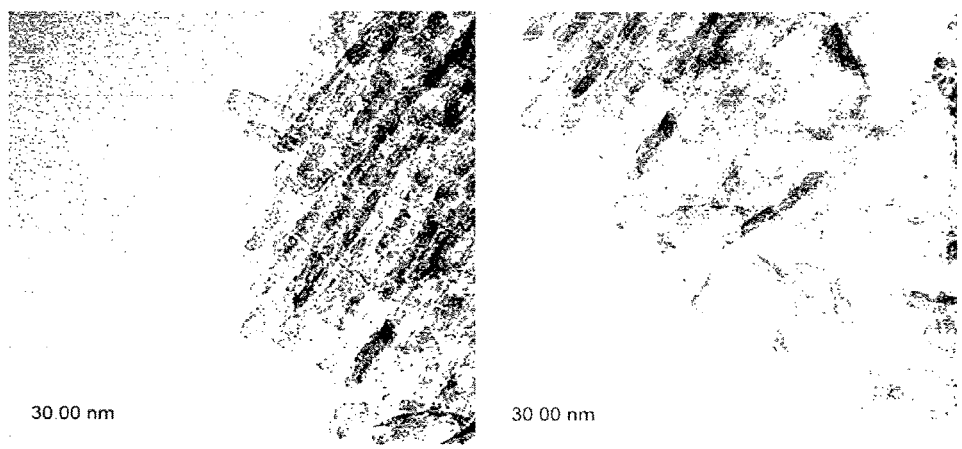
FIG. 15 shows TEM images of the 13-day product of Example 9.

Example 2 was repeated except that the fumed alumina was pre-dissolved in the hydroxide sources before the addition of the Ludox AS-40. The pre-dissolution was carried out in a similar manner to that described in Example 7. The crystallization was significantly slower when the aluminum was completely dissolved; requiring 13 days (instead of 3) to obtain the product with the powder XRD pattern shown at the bottom of FIG. 13. The middle trace shows the powder diffraction pattern after 15 days, and the top trace shows the powder pattern of a typical sample of COK-5. FIG. 14 shows SEM images of the 13-day product, while FIG. 15 shows TEM images of the same product. TEM shows that the lengths of the crystals are generally between 10 and 50 nm and the widths of the crystals are generally 4-10 nm in size. After the crystals are microtomed and examined by TEM, it is found that the crystals are generally about 4 nm in thickness. $^{27}$Al MAS NMR indicates that all of the aluminum in both the 13-day product and the 15-day product is in a tetrahedral coordination.

The 15-day product was then calcined in a muffle furnace by heating in a nitrogen stream from ambient temperature to 400° C. over a two hour period, maintaining this temperature for 15 minutes, switching the gas stream to air, increasing the temperature from 400° C. to 600° C. over a two hour period, maintaining the temperature at 600° C. for 2 hours, and then allowing the furnace to cool to ambient conditions. After calcination, the sample was ammonium-exchanged in a solution created by dissolving an equal mass ammonium nitrate (to that of the zeolite) in a 10-fold mass of the zeolite. The zeolite/ammonium nitrate suspension was heated overnight in a steambox at 98° C. The zeolite was then isolated by filtration, washed thoroughly with deionized water, and allowed to dry overnight in a vacuum oven at 60° C. The zeolite was then calcined to 500° C. to convert it to the acidic form. The surface area of the sample was then measured using nitrogen physisorption. Analysis of the physisorption data by the t-plot method shows that this material possesses an external surface area of 314 m$^2$/g and an internal surface area of 314 m$^2$/g (0.135 cc/g micropore volume), i.e., for this sample half of the measured surface area is due to the external surface of the crystallites.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated. The term "comprising" is synonymous with the term "including". Likewise whenever a composition, an element or a group of components is preceded with the transitional phrase "comprising", it is understood that we also contemplate the same composition or group of components with transitional phrases "consisting essentially of", "consisting of", "selected from the group of consisting of", or "is" preceding the recitation of the composition, component, or components, and vice versa.

The invention claimed is:

1. A molecular sieve having the structure of COK-5, comprising in its pores at least one diquaternary ammonium compound selected from the group consisting of 1,4-bis(N-propylpyrrolidinium)butane dications, 1,4-bis(N-butylpyrrolidinium)butane dications and 1,5-bis(N-propylpyrrolidinium)pentane dications.

2. The molecular sieve of claim 1, further comprising crystals having an external surface area as determined by the t-plot method for nitrogen physisorption of about 100 to about 300 m$^2$/g.

3. The molecular sieve of claim 1, further comprising crystals having a total surface area as determined by the t-plot method for nitrogen physisorption of about 350 to about 650 m$^2$/g.

4. The molecular sieve material of claim 1 having a composition comprising the molar relationship:

$$mQ:(n)YO_2: X_2O_3,$$

wherein 0<m/n ≤0.2, n is at least 20, 0<m≤0.2n, Q is said at least one diquaternary ammonium compound, X is a trivalent element and Y is a tetravalent element.

5. The molecular sieve material of claim 4, the tetravalent element Y comprises silicon and the trivalent element X comprises boron or aluminum.

6. A molecular sieve having the structure of COK-5 having an X-ray diffraction pattern with a first composite peak with a maximum at 25.0 (±0.30) degrees 2-theta (2θ) which has an intensity above background of Imax$_A$ and which intersects a second composite peak with a maximum at 23.0 (±0.20) degrees 2-theta (2θ) to form a local minimum which has an intensity above background of Imin$_A$, such that the Imin$_A$/Imax$_A$ ratio is >0.7.

7. A molecular sieve having the structure of COK-5, comprising crystals having an external surface area as determined by the t-plot method for nitrogen physisorption of at least 100 m$^2$/g and having an X-ray diffraction pattern with a single diffuse composite feature in the 2-theta (2θ) range from 21.5 to 25.5 degrees.

8. The molecular sieve of claim 7, comprising crystals having a total surface area as determined by the t-plot method for nitrogen physisorption of at least 350 m$^2$/g.

9. A process for producing a molecular sieve having the structure of COK-5, the process comprising:
(i) preparing a synthesis mixture capable of forming said molecular sieve, said mixture comprising a source of an alkali metal (M), a source of an oxide of a tetravalent element (Y), a source of a trivalent element (X), water, and a directing agent (Q) comprising one or more of 1,4-bis(N-propylpyrrolidinium)butane dications, 1,4-bis(N-butylpyrrolidinium)butane dications or 1,5-bis(N-propylpyrrolidinium)pentane dications, and said mixture having a composition, in terms of mole ratios, within the following ranges:
YO$_2$/X$_2$O$_3$ at least 20;
H$_2$O/YO$_2$ about 20 to about 60;
M/YO$_2$ about 0.1 to about 0.5;
OH$^{31}$/YO$_2$ about 0.2 to about 0.6; and
Q/YO$_2$ about 0.04 to about 0.25;
(ii) heating said mixture under crystallization conditions at a heating temperature of from about 125° C. to about 200° C. and a length of time from about 1 day to about 21 days until crystals of said molecular sieve are formed; and
(iii) recovering said crystals of said molecular sieve from step (ii).

10. The process of claim 9, wherein the tetravalent element Y comprises silicon and the trivalent element X comprises aluminum.

11. The process of claim 9, wherein the tetravalent element Y comprises silicon and the trivalent element X comprises boron.

12. A molecular sieve material produced by the process of claim 9.

13. A process for converting a feedstock comprising an organic compound to a conversion product which comprises contacting said feedstock at organic compound conversion conditions with a catalyst comprising an active form of the molecular sieve of claim 1.

\* \* \* \* \*